United States Patent [19]

Mueller et al.

[11] Patent Number: 5,145,992

[45] Date of Patent: Sep. 8, 1992

[54] PROCESS AND PREPARATION OF α-ALKOXY ACETIC ACIDS AND THEIR SALTS

[75] Inventors: Richard A. Mueller, Glencoe; Richard A. Partis, Evanston, both of Ill.

[73] Assignee: G. D. Searle & Co., Chicago, Ill.

[21] Appl. No.: 695,676

[22] Filed: May 6, 1991

[51] Int. Cl.$^5$ .................. C07C 319/20; C07C 51/09
[52] U.S. Cl. ........................... 562/431; 560/17; 560/55; 560/59; 560/61; 562/401; 562/465; 562/469; 562/471; 562/472; 568/46
[58] Field of Search ............. 562/431, 465, 469, 471, 562/472; 560/17, 55, 59, 61, 401

[56] References Cited

U.S. PATENT DOCUMENTS

| | | | |
|---|---|---|---|
| 3,255,241 | 6/1966 | Schultz et al. | 562/431 |
| 3,918,899 | 11/1975 | Perrier et al. | 8/120 |
| 4,711,903 | 12/1987 | Mueller et al. | 514/381 |
| 4,755,524 | 7/1988 | Mueller et al. | 514/381 |
| 4,804,777 | 2/1989 | Sumner, Jr. et al. | 562/421 |

OTHER PUBLICATIONS

Abraham, et al., *J. Med. Chem.*, 27:1549-1599, (1984).
Taylor, et al., *J. Org. Chem.*, 53:35-38, (1988).
Fuson, et al., *Organic Synthesis Collected Volumes*, 2:260-262, (1943).

Primary Examiner—Jose G. Dees
Assistant Examiner—Vera C. Clarke
Attorney, Agent, or Firm—Mary Jo Kanady; Paul D. Matukaitis

[57] ABSTRACT

A process for producing an α-alkoxy acetic acids and salts thereof which comprises reacting an alcohol of the formula

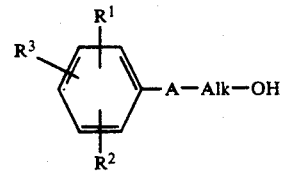

wherein $R^1$, $R^2$ and $R^3$ can be hydrogen, alkyl, alkoxy, halo, phenyl, substituted phenyl, or hydroxy; A can be S, O or —$CH_2$—; and Alk is straight or branched chain alkylene, with a base in an aprotic solvent, then reacting the resulting alkoxide with a monohaloacetic acid ester to give an alkoxyacetate followed by reaction of the alkoxyacetate with a hydrogen halide, organic acid or Lewis acid in nitromethane to give the corresponding α-alkoxyacetic acid which then may be recovered or may optionally be converted to the corresponding salt by contracting the α-alkoxyacetic acid with a base.

21 Claims, No Drawings

PROCESS AND PREPARATION OF α-ALKOXY ACETIC ACIDS AND THEIR SALTS

BACKGROUND OF THE INVENTION (a) Field of the Invention

The present invention relates to a novel process for the preparation of an α-alkoxy acetic acid having the general formula

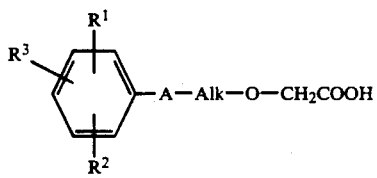

or a salt thereof, wherein $R^1$, $R^2$ and $R^3$ are the same or different and are hydrogen, alkyl, alkoxy, halo, phenyl, substituted phenyl, or hydroxy; A is sulfur, oxygen, or —$CH_2$—; and Alk is straight or branched chain alkylene; which comprises reacting a compound of the formula

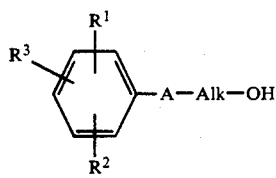

wherein $R^1$, $R^2$, $R^3$, A, and Alk are defined as above, with a suitable base in an aprotic organic solvent followed by reaction of the resulting alkoxide with a tert-alkyl monohaloacetic acid ester to generate an alkoxyacetate ester which is then reacted with an appropriate hydrogen halide, organic acid or Lewis acid in nitromethane to give the α-alkoxy acetic acid product. Reaction of this product with an appropriate base gives an α-alkoxyacetic acid salt.

The process of the present invention is especially useful for preparing phenylthio-α-alkoxy acetic acids. This process is also especially useful for preparing single isomers of the products because one or more chiral centers contained within the Alk chain or the A function are not disturbed by this basic process. In some cases, chiral compounds are preferred over the racemic or enantiomeric mixtures for pharmaceutical or other uses. Therefore, processes which aid in the preparation of single isomers are very advantageous.

(b) Background Information

U.S. Pat. Nos. 4,711,903 and 4,755,524 disclose a method of preparing a [2-[[3,5-bis(1,1-dimethylethyl)-4-hydroxyphenyl]thio]-alkoxy]acetic acid from a 2,6-bis (1,1-dimethylethyl)-4-[(2-hydroxyalkyl) thio]phenol by a process in which chloroacetic acid is added to the alcohol in t-butyl alcohol which is a protic solvent, then potassium tert-butoxide is added, and the mixture is refluxed. This method gives yields of less than 5% and thus is not a very efficient process.

U.S. Pat. No. 4,804,777 discloses a process for the preparation of an aryloxy acetic acid by oxidation of an aryloxyethanol in an aqueous alkaline reaction medium at a temperature in the range of 0° C. to the boiling point of the reaction medium in the presence of a catalytic amount of a catalyst comprised of palladium, silver, and optionally antimony, and carbon to form the corresponding alkali metal ester and contacting the alkali metal with a mineral acid. Metal catalysts can scramble hydrogen atoms or carbon atoms and chirality can be lost. In addition, they can either abstract or be poisoned by sulfur.

U.S. Pat. No. 3,918,899 discloses a method of preparing carboxymethylated cottons in non-aqueous media by reacting anhydrous sodium cellulosate with a salt of a monochloroacetate in an anhydrous DMSO solution.

R. C. Fuson and B. H. Wojcik, ORGANIC SYNTHESIS COLLECTED VOLUMES, 2:260–262(1943) discloses a three-step method for preparing ethoxyacetic acid from ethanol which is the substrate and the solvent (protic solvent).

D. J. Abraham, et al., J. MED. CHEM., 27:1549–1559 (1984) discloses alkylation of the phenolic hydroxyl group in 2-hydroxy-4-nitromethylbenzoate by reacting it with $BrCH_2COO$-Bu-t in the presence of NaH in tetrahydrofuran (THF). Phenolic hydroxyl groups are acidic.

E. C. Taylor, et al., J. ORG. CHEM. 53:35–38 (1988) at page 36 discloses selective removal of a tert-butyl ester from a pterin of the formula

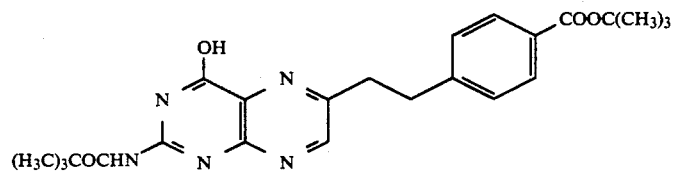

using gaseous hydrogen chloride in nitromethane to give 2-pivaloyl-10-deazapteroic acid having the formula

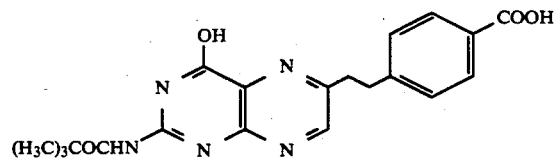

SUMMARY OF THE INVENTION

The present invention relates to a process for preparing an α-alkoxy acetic acid of formula I or a salt thereof

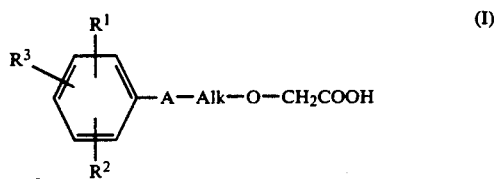

wherein $R^1 R^2$ and $R^3$ are the same or different and are hydrogen, alkyl, lower alkoxy, halo, phenyl, substituted phenyl, or hydroxy; A is sulfur, oxygen, or —CH$_2$—; and Alk is straight or branched chain lower alkylene; which comprises reacting a compound of the formula

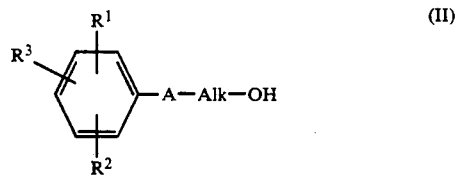

(II)

wherein $R^1$, $R^2$, $R^3$, A, and Alk are defined as hereinbefore with a base in an aprotic organic solvent followed by reaction of the resulting alkoxide with a tert-alkyl monohaloacetic acid ester to form an alkoxyacetate and then reacting the alkoxyacetate with a hydrogen halide in nitromethane to give the α-alkoxy acetic acid of formula I then optionally reacting the α-alkoxy acetic acid with a base to give an α-alkoxy acetic acid salt.

DETAILED DESCRIPTION OF THE INVENTION

The present invention relates to a process for preparing an α-alkoxy acetic acid of the formula (I)

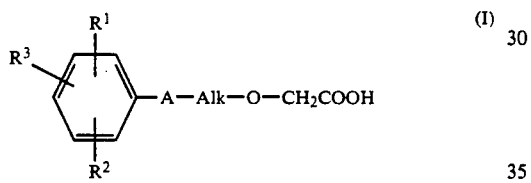

(I)

wherein $R^1$, $R^2$ and $R^3$ are the same or different and are hydrogen, alkyl of 1 to 10 carbon atoms, alkoxy of 1 to 4 carbon atoms halo, phenyl, substituted phenyl, or hydroxy; A is sulfur, oxygen, or —CH$_2$—; and Alk is straight or branched chain alkylene having from 2 to 6 carbon atoms; which comprises:

(a) reacting a compound of the formula

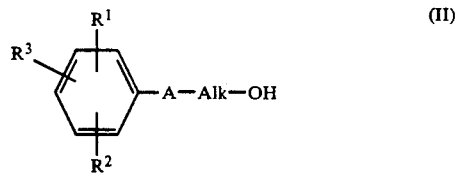

(II)

wherein $R^1$, $R^2$, $R^3$, A, and Alk are defined as hereinbefore with a base in an aprotic organic solvent;

(b) reaction of the resulting alkoxide with a tert-butyl monohaloacetate to form a tert-butyl alkoxyacetate;

(c) reacting the tert-butyl alkoxy acetate with hydrogen chloride in nitromethane to give the α-alkoxy acetic acid product; and (d) optionally reacting the α-alkoxy acetic acid with a base to give an alkoxy acetic acid salt.

Steps (a) and (b) are conducted in the same reaction vessel. The starting compound of Formula (II) is added to the base in the aprotic solvent and allowed to react, then the tert-butyl monohaloacetate is added and the reaction is allowed to proceed.

An advantage of the process of the present invention is that in this process the tert-butyl monohaloacetic acid ester does not react with the sulfur in those compounds wherein A is sulfur.

If the α-alkoxy acetic acid salt is desired it can be made by reacting the α-alkoxy acetic acid with an appropriate base such as sodium hydroxide, potassium hydroxide, lithium hydroxide and the like.

The present invention also relates to a process for preparing a compound of the formula (III)

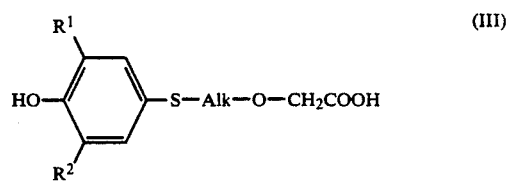

(III)

or a salt thereof, wherein $R^1$ and $R^2$ are the same or different and are alkyl of 1 to 10 carbon atoms, halo, phenyl, or substituted phenyl; and Alk is straight or branched chain alkylene having 2 to 6 carbon atoms; which comprises:

(a) reacting a compound of the formula

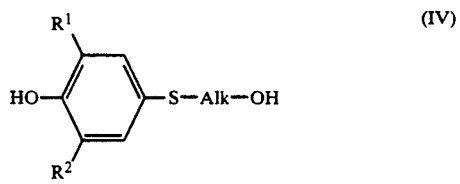

(IV)

wherein $R^1$, $R^2$ and Alk are defined as hereinbefore with a base in an aprotic organic solvent;

(b) reacting the resulting alkoxide with a tert-butyl monohaloacetate to form a tert-butyl alkoxyacetate;

(c) reacting the tert-butyl alkoxyacetate with hydrogen chloride in nitromethane to give the α-alkoxy acetic acid; and (d) optionally reacting the α-alkoxy acetic acid with a base to give an α-alkoxy acetic acid salt.

The process of the present invention is particularly useful for preparing compounds of Formula III wherein $R^1$ and $R^2$ represent tert-alkyl.

Other advantages of the process of the present invention are chiral centers are preserved, the sulfur atom is not attacked or removed, the conditions are non-oxidizing and chromatography is not necessarily required but may be used if desired. Only one transfer of reactants is required to produce fine chemicals. Example 4 describes one example of how the process of the present invention can be used to obtain the product without the necessity for using chromatography.

In a preferred embodiment the process of the present invention can be used to prepare a compound of the formula

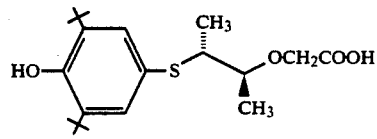

or salt thereof, by (a) reacting a compound of the formula

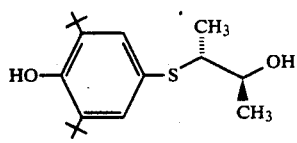

with a base such as sodium hydride in an aprotic organic solvent such as tetrahydrofuran;

(b) reacting the resulting alkoxide with a monohaloacetic acid ester such as tert-butyl-2-bromoacetate to form an α-alkoxy acetic acid ester of the formula

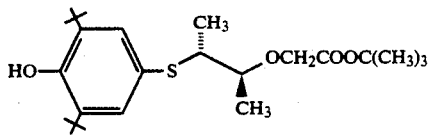

(c) reacting the α-alkoxyacetic acid ester with hydrogen chloride in nitromethane to form an α-alkoxy acetic acid; and (d) optionally reacting the α-alkoxyacetic acid with a base to form an α-alkoxyacetic acid salt.

Aprotic organic solvents suitable for use in the present invention include but are not limited to tetrahydrofuran (THF), ethers such as ethyl ether, t-butylmethyl ether, diisopropyl ether, and dioxane or dipolar aprotic solvents such as dimethylformamide (DMF) or hexamethylphosphoramide (HMPA). Tetrahydrofuran is a preferred solvent.

Suitable tert-alkyl monohaloacetic esters for use in the process of the present invention include tert-butyl-2-bromoacetate, tert-butyl-2-chloroacetate or tert-butyl-2-iodoacetate.

Suitable mineral acids (dry, i.e., hydrogen halides), organic acids, or Lewis acids for deprotecting the alkoxy acetate ester to give the acid include but are not limited to hydrogen chloride, hydrogen bromide, hydrogen fluoride, sulfuric acid, acetic acid, trifluoroacetic acid, methanesulfonic acid, trifluoromethanesulfonic acid, phosphoric acid, boron trifluoride, and boron trifluoride etherate. Hydrogen chloride is preferred.

Suitable bases for reacting with the alcohol of Formula II include but are not limited to sodium hydride, potassium hydride, potassium hexamethyldisilazane (KHMDS), lithium hexamethyldisilazane (LiHMDS), sodium hexamethyldisilazane (NaHMDS) calcium hydride, alkyllithium reagents such as n-butyl lithium, lithium dialkylamides, lithium bis (trimethylsilyl) amide, sodium bis (trimethylsilyl) amide, and potassium bis (trimethylsilyl) amide. Sodium hydride is a preferred base. The reaction of the alcohol and base can be conducted over a broad temperature range, preferably from about −75° C. to about 50° C. and most preferably from about −75° C. to about −10° C.

Co-solvents such as methylene chloride, chloroform, carbon tetrachloride, tetrahydrofuran, and dioxane can be used with nitromethane.

The relative amounts of reactants used in the process can vary. Preferably an excess of base is reacted with the alcohol. In general the mole ratio of base to alcohol can be about 2 to 4 moles of base to about 1 mole of alcohol, preferably about 3.1 moles of base to about 1.0 moles of alcohol or alcohol equivalent such as an additional —OH group. In general, an excess of monohaloacetic acid ester is reacted with the alkoxide although the reaction can be conducted as a 1:1 molar ratio. Preferably, about 1.1 moles of monohaloacetic acid ester is reacted with the alkoxide intermediate.

The addition of a monohaloacetic acid ester such as t-butylbromoacetate can also be conducted over a broad temperature range, preferably from about −75° C. to about 50° C. and most preferably from about −75° C. to about 0° C. The de-esterification of the alkoxyacetate with an acid in nitromethane may be conducted over a broad temperature range, preferably from about −70° C. to about 25° C. (Room Temperature) with about −30° C. to about 0° C. most preferred. The alkoxy acetate salt can be acidified to the acid over a broad temperature range, preferably from about 0° C. to about 50° C.

The term "alkyl", as used herein, refers to straight or branched chain alkyl groups having from 1 to 10 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The term "lower alkylene", as used herein, refers to straight or branched chain lower alkylene groups having from 1 to 6 carbon atoms, i.e., methylene, ethylene, n-propylene, iso-propylene, n-butylene, sec-butylene, tert-butylene, 3-methylpentylene, 2-methylbutylene, 1,1-dimethylethylene, and the like.

The term "substituted phenyl" refers to phenyl having one or more substituents selected from the group consisting of halo, hydroxy, phenyl, lower alkyl and lower alkoxy.

The term "halo", as used herein in reference to phenyl substituents includes chloro, bromo, iodo and fluoro.

The term "lower alkoxy" refers to alkoxy groups having from 1 to 6 straight or branched chain carbon atoms, i.e., methoxy, propoxy, tert-butoxy, pentoxy, etc.

The term "tert-alkyl" as used herein in reference to $R_1$ and $R_2$ refers to branched chain alkyl moieties of from about 4 to 10 carbon atoms having a tertiary carbon atom attached to the phenyl ring substituted by $R_1$ and $R_2$. Examples of such groups are tert-butyl, i.e., 1,1-dimethylethyl, 1-1-dimethylpropyl, 1-methyl-1-(ethyl) pentyl, 1,1-diethylpropyl, 1-ethyl-1-(propyl)butyl and the like.

Scheme A illustrates the use of the process of the present invention for the preparation of substituted phenyl α-alkoxy acetic acids of Formula I in which $R^1$, $R^2$, $R^3$, A and Alk are defined as hereinbefore from alcohols of Formula II by: reacting the alcohol (II) with a base such as sodium hydride in an aprotic organic solvent such as tetrahydrofuran (THF) to form an alkoxide followed by coupling of the resulting alkoxide with an ester of a monohaloacetic acid such as tert-butyl monobromoacetate to form the α-alkoxy-acetate ester (IIa) which is converted to the acid (I) by reaction with gaseous hydrogen chloride in nitromethane.

Scheme B illustrates the preparation of (3,5-disubstituted-4-hydroxyphenyl)thio-α-alkoxy acetic acids of Formula III wherein $R^1$, and $R^2$ are alkyl of 1 to 10 carbon atoms, halo, phenyl or substituted phenyl and A and Alk are defined as hereinbefore from alcohols of Formula IV by the process of the present invention.

The present invention is particularly useful for preparing (±)[2S*-[[3,5-bis(1,1-dimethylethyl)-4-hydroxyphenyl]thio]-1R*-methylpropyoxy]acetic acid (Formula V) which is a 5-lipoxygenase inhibiting compound and is useful in the treatment of inflammation, allergy, and hypersensitivity reactions. Scheme C illustrates the preparation of this compound by reacting (±)2,6-bis(1,1-dimethylethyl)-4-[(2S*-hydroxy-1R*-methylpropyl)thio]phenol (Formula VI) with sodium hydride in THF followed by reaction of the resulting alkoxide with tert-butyl monobromoacetate to form the alkoxyacetate ester which is then reacted with hydrogen chloride in nitromethane to give the product. Yields of 25% and greater can be obtained using this process.

SCHEME A (II)

R³—⟨R¹ ring R²⟩—A—Alk—OH

1. NaH/THF
2. BrCH₂COOtBu
↓

(IIa)

R³—⟨R¹ ring R²⟩—A—Alk—OCH₂COOC(CH₃)₃

HCl/CH₃NO₂
↓

(I)

R³—⟨R¹ ring R²⟩—A—Alk—O—CH₂COOH

SCHEME B (IV)

HO—⟨R¹ ring R²⟩—S—Alk—OH

1. NaH/THF
2. BrCH₂COOtBu
↓

HO—⟨R¹ ring R²⟩—S—Alk—OCH₂COOC(CH₃)₃

HCl/CH₃NO₂
↓

-continued
SCHEME B (III)

HO—⟨R¹ ring R²⟩—S—Alk—O—CH₂COOH

SCHEME C (VI)

HO—⟨t-Bu ring t-Bu⟩—S—CH(Me)—CH(Me)—OH

1. NaH/THF
2. BrCH₂COOtBu
↓

HO—⟨t-Bu ring t-Bu⟩—S—CH(Me)—CH(Me)—O—CH₂—C(=O)—O—t-Bu

HCl/CH₃NO₂
↓

(V)

HO—⟨t-Bu ring t-Bu⟩—S—CH(Me)—CH(Me)—O—CH₂—C(=O)—OH

The following examples further illustrate the invention. All temperatures are degrees Celsius unless otherwise noted.

EXAMPLE 1

(±)2,6-Bis(1,1-dimethylethyl)-4-((2S*-hydroxy-1R*-methylpropyl)thio]phenol

HO—⟨ring⟩—S—CH(CH₃)—CH(OH)—CH₃

An argon-purged vessel was charged with 54 L of anhydrous methanol which was then purged with argon for 5 min. About 12 L of methanol was distilled off at atmospheric pressure, and the remaining methanol was transferred to pressure cans under argon. The dry, argon-purged vessel was charged with 3.03 kg of sodium methoxide followed by 29.7 kg of methanol from the pressure cans. The mixture was stirred for 10 min, and 6.7 kg of 2,6-bis(1,1-dimethylethyl)-4-mercaptophenol was added in small portions under argon. The mixture was stirred for 1 h at room temperature and cooled to 0° C. at which point 2.23 kg of trans-2,3-epoxybutane was added followed by a 2.7 kg methanol rinse. The mixture was stirred at 0° C. for 4 h and then at less than 25° C. for 16 h. When the reaction was complete as indicated by thin layer chromatography, the reaction mixture was added to 59 L of IN hydrochloric acid, and the aqueous solution was extracted twice with a total of 89 L of ethyl acetate. The combined organic phase was washed once with 34 L of dilute aqueous sodium chloride solution and once with 13 L of saturated aqueous sodium chloride solution. The organic phase was dried over 3.5 kg of anhydrous magnesium sulfate and filtered. The solvent was removed by distillation under reduced pressure. The crude product was dissolved in 6.7 L of refluxing n-hexane, and the solution was cooled to 5° C. The solid was collected by filtration, washed with cold (about 0° C.) n-hexane and dried at 50° C. in a vacuum oven to give 7.44 kg (85% of theory) of (±)2,6-bis(1,1-dimethylethyl)-4-[(2S*-hydroxy-1R*-methylpropyl)thio]phenol.

EXAMPLE 2

(±)tert-Butyl[2S*-[[3,5-bis(1,1-dimethylethyl)-4-hydroxyphenyl]thio]-1R*-methylpropoxy]acetate

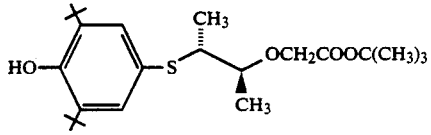

Into a dry reaction vessel is charged 22.76 g of sodium hydride under inert atmosphere. The hydride is washed with 300 ml of hexane and the hexane wash is removed via cannula. To the hydride is added 800 ml of tetrahydrofuran (THF) and the mixture is cooled to −75° C. A solution of 95 g of (±)2,6-bis(1,1-dimethylethyl)-4-[2S*-hydroxy-1R*-methylpropyl)thio]phenol in 200 ml of THF is added and the mixture is allowed to warm to 0° C. for 1 hour. The mixture is cooled back to −75° C. and 65.65 g of t-butyl bromoacetate is added via syringe. The mixture is warmed to room temperature and stirred for 6 hours. The product is poured directly into a solution of 1600 ml of ice water and 160 ml of acetic acid. The solution is extracted with 2400 ml of ethyl acetate, dried (mg SO4), filtered, and the solvent is removed under reduced pressure to give 133.4 g of crude oil. The product is purified on a silica gel column (ethyl acetate/hexane gradient) to give 84.4 g (65% yield) of (±)tert-butyl[2S*-[[3,5-bis(1,1-dimethylethyl)-4-hydroxyphenyl]thio]-1R*-methylpropoxy]acetate.

EXAMPLE 3

(±)[2S*-[[3,5-Bis(1,1-dimethylethyl)-4-hydroxyphenyl]thio]-1R*-methylpropoxy]acetic acid

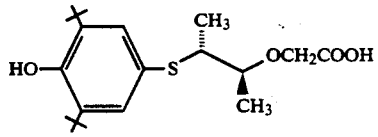

Into a dry reaction vessel is charged 29.89 g of (±)tert butyl(±)[2S*-[[3,5-bis(1,1-dimethyl-ethyl)-4-hydroxyphenyl]thio]-1R*-methylpropoxy]acetate and 350 ml of nitromethane. The mixture is cooled to 0°-5° C. A solution of 5.2 g of anhydrous hydrogen chloride in 160 ml of nitromethane at 0°-5° C. is added, and the reaction mixture is stirred for 4 hours. The product is washed 4 times with 350 ml pentane. The nitromethane layer is concentrated under reduced pressure and triturated with 900 ml hexane. The hexane solution is concentrated under reduced pressure to an oil. The crude oil is purified on a silica gel column eluting with 20% ethyl acetate/79% hexane/1% acetic acid to give 11.22 g of pure oil which is crystallized with hexane to give 13.1 g (50% yield) of (±)[2S*-[[3,5-bis(1,1-dimethyl-ethyl)-4hydroxyphenyl]thio]-1R*-methylpropoxy]acetic acid.

EXAMPLE 4

(±)[2S*-[[3,5-Bis(1,1-dimethylethyl)-4-hydroxyphenyl]thio]-1R*-methylpropoxy]acetic acid

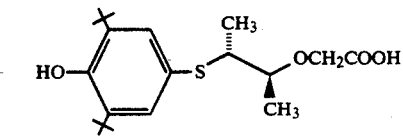

Into a dry vessel was charged 1.4 g of sodium hydride (60% dispersion in mineral oil) under an inert atmosphere (argon). The hydride was washed twice with heptane (25 ml) and once with tetrahydrofuran (15 ml) with the wash removed by cannula. Tetrahydrofuran (100 ml) was added and the mixture cooled to −70° C. A solution of 3.5 g of (±)2,6-bis(1,1-dimethylethyl)-4-[2S*-hydroxy-1R*-methylpropyl)thio]phenol in 25 ml tetrahydrofuran was added, and the mixture was allowed to warm to −10° C. for 1 hour The mixture was cooled to −75° C. and 2.2 g of t-butyl bromoacetate was added via syringe. The mixture was allowed to warm slowly to room temperature and stirred for 6 hours. The reaction mixture was cooled to 0° C. with an ice bath, poured directly into 5% acetic acid (100 ml) and stirred for 30 min. Water (100 ml) was added and the (±) tert-butyl[2S*-[[3,5-bis(1,1-dimethylethyl)-4-hydroxyphenyl]thio]-1R*-methylpropoxy]acetate was extracted into ethyl acetate (2×75 ml), dried (Na2SO4), filtered, and the solvent was removed under reduced pressure to give 4.9 g of material.

This material was dissolved in 50 ml of nitromethane and cooled to 0° C. A solution of 0.40 g of anhydrous hydrogen chloride in 11 ml of nitromethane at 0° C. was added, and the solution was stirred cold for 6.5 hours and stored in the refrigerator for 20 hours. The nitromethane was removed under reduced pressure to give 4.6 g of an orange oil. This oil was dissolved in 250 ml hexane and washed with a solution of 50 ml saturated sodium bicarbonate in 100 ml water. A small amount of ethyl acetate was added to facilitate the separation. The organic layer was washed first with sodium bicarbonate (50 ml) and second with sodium carbonate (50 ml). Each of the aqueous base layers were acidified with 10% hydrochloric acid and extracted with ethyl acetate. The combined ethyl acetate solution was dried (Na2SO4), filtered, and the solvent was removed under reduced pressure to give 2.0 g of an oil (45% yield) which is crystallized with hexane to give 1.2 g(29% yield) of (±) [2S*-[[3,5-bis(1,1-dimethylethyl)-4-hydroxyphenyl]thio]-1R*-methylpropoxy]acetic acid.

Analysis calcd. for $C_{20}H_{32}O_4S$ (368.54): C, 65.18; H, 8.75; S, 8.70. Found: C, 64.81; H, 8.79; S, 8.67.

What is claimed is:

1. A process for preparing a compound of the formula

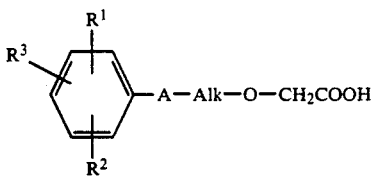 (I)

or a salt thereof, wherein $R^1$, $R^2$ and $R^3$ are the same or different and are hydrogen, alkyl of 1 to 10 carbon atoms, lower alkoxy, halo phenyl, substituted phenyl having one or more substituents selected from the group consiting of halo, hydroxy, phenyl, lower alkyl and lower alkoxy, or hydroxy; A is sulfur, oxygen, or —$CH_2$—; and Alk is straight or branched chain lower alkylene; which comprises:

(a) reacting a compound of the formula

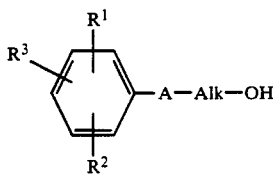

wherein $R^1$, $R^2$, $R^3$, A, and Alk are defined as hereinbefore with a base in an aprotic organic solvent;

(b) reacting the resulting alkoxide with a tert-alkyl monohaloacetic acid ester to form an alkoxyacetate; and (c) reacting the alkoxyacetate with hydrogen chloride in nitromethane to given an α-alkoxyacetic acid; and (d) optionally reacting the α-alkoxyacetic acid with a base to give an α-alkoxyacetic acid salt.

2. A process according top claim 1 for preparing a compound of the formula:

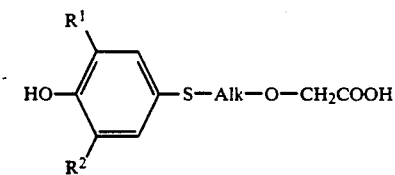

or a salt thereof wherein $R^1$ and $R^2$ are the same or different and are tert-alkyl of 4 to 10 carbon atoms, halo, phenyl, or substituted phenyl having one ore more substituents selected from the group consisting of halo, hydroxy, phenyl, lower alkyl and lower alkoxy; and Alk is straight or branched chain alkyl having 1 to 6 carbon atoms; which comprises:

(a) reacting a compound of the formula

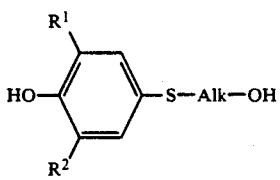

wherein, $R^1$, $R^2$, and Alk are defined as hereinbefore, with a base in an aprotic organic solvent;

(b) reacting the resulting alkoxide with a tert-alkyl monohaloacetic acid ester to form an alkoxyacetate; and (c) reacting the alkoxyacetate with hydrogen chloride in nitromethane to give the α-alkoxyacetic acid; and (d) optionally reacting the α-alkoxyacetic acid with a base to give an α-alkoxyacetic acid salt.

3. A process according to claim 1 wherein A is sulfur.

4. A process according to claim 2 wherein $R^1$ and $R^2$ are tert-alkyl.

5. A process according to claim 4 wherein $R^1$ and $R^2$ are tert-butyl.

6. A process according to claim 2 wherein $R^1$ and $R^2$ are phenyl or substituted phenyl having one or more substituents selected from the group consisting of halo, hydroxy, phenyl, lower alkyl and lower alkoxy.

7. A process according to claim 2 wherein $R^1$ and $R^2$ are halo.

8. A process according to claim 1 wherein the aprotic organic solvent is tetrahydrofuran.

9. A process according to claim 2 wherein the aprotic organic solvent is tetrahydrofuran.

10. A process according to claim 8 wherein the tert-alkyl ester of a monohaloacetic acid is t-butyl bromoacetate.

11. A process according to claim 9 wherein the tert-alkyl ester of a monohaloacetic acid is t-butyl bromoacetate.

12. A process according to claim 11 wherein the base is sodium hydride.

13. A process according to claim 2 for preparing a compound of the formula

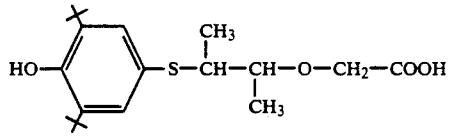

which comprises:

(a) reacting an alcohol of the formula

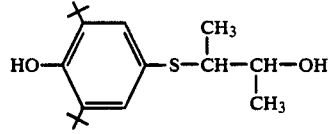

with a base in an aprotic organic solvent;

(b) reacting the resulting alkoxide with a tert-alkyl monohaloacetic acid ester to form an alkoxyacetate; and (c) reacting the alkoxyacetate with hydrogen chloride in nitromethane to form the α-alkoxyacetic acid.

14. A process according to claim 13 wherein the aprotic organic solvent is tetrahydrofuran.

15. A process according to claim 14 wherein the tert-alkyl monohaloacetic acid ester is t-butyl bromoacetate.

16. A process according to claim 13 for preparing a compound of the formula

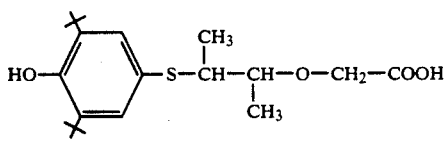

which comprises:

(a) reacting an alcohol of the formula

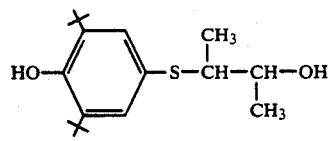

with sodium hydride in tetrahydrofuran;

(b) reacting the resulting alkoxide with t-butyl bromoacetate to form an alkoxyacetate; and (c) reacting the alkoxyacetate with hydrogen chloride in nitromethane to form the α-alkoxyacetic acid.

17. A process to claim 15 for preparing a compound of the formula

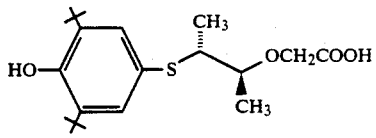

which comprises:

(a) reacting an alcohol of the formula

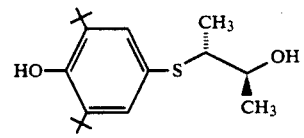

with a base in an aprotic organic solvent;

(b) reacting the resulting alkoxide with a tert-alkyl monohaloacetic acid ester to form an alkoxyacetate; and (c) reacting the alkoxyacetate with hydrogen chloride in nitromethane to form the α-alkoxyacetic acid.

18. A process according to claim 17 wherein the base is sodium hydride.

19. A process according to claim 17 wherein the aprotic organic solvent is tetrahydrofuran.

20. A process according to claim 17 wherein the tert-alkyl monohaloacetic acid ester is t-butyl bromoacetate.

21. A process according to claim 17 for preparing a compound of the formula

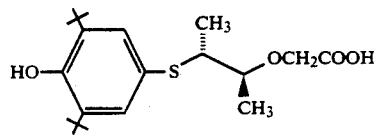

which comprises:

(a) reacting an alcohol of the formula

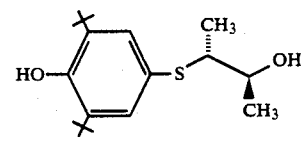

with sodium hydride in tetrahydrofuran;

(b) reacting the resulting alkoxide with t-butyl bromoacetate to form an alkoxyacetate; and (c) reacting the alkoxyacetate with hydrogen chloride in nitromethane to form the α-alkoxyacetic acid.

* * * * *

UNITED STATES PATENT AND TRADEMARK OFFICE
CERTIFICATE OF CORRECTION

PATENT NO. : 5,145,992
DATED     : September 8, 1992
INVENTOR(S) : Mueller, et al.

It is certified that error appears in the above-identified patent and that said Letters Patent is hereby corrected as shown below:

Column 8, line 47, reading "2.6-Bis(1.1", should read -- 2,6-Bis(1,1 --.

Column 9, line 5, reading "IN" should read -- 1N --.

Column 9, line 66, reading "-4hydroxyphenyl" should read -- -4-hydroxyphenyl --.

Column 10, line 12, reading "4hydroxyphenyl" should read -- 4-hydroxyphenyl --.

Column 10, line 34, reading "hour" should read -- hour. --.

Column 11, line 16, reading "consiting" should read -- consisting --.

Column 11, line 54, reading "ore" should read -- or --.

Column 13, line 34, reading "A process to claim 15" should read -- A process according to claim 13 --.

Signed and Sealed this

Eighth Day of March, 1994

Attest:

BRUCE LEHMAN

Attesting Officer    Commissioner of Patents and Trademarks